US010327946B2

(12) United States Patent
de Sousa Martins et al.

(10) Patent No.: US 10,327,946 B2
(45) Date of Patent: *Jun. 25, 2019

(54) INTRAOCULAR DELIVERY OF BIOACTIVE MOLECULES USING IONTOPHORESIS

(71) Applicant: Kemin Industries, Inc., Des Moines, IA (US)

(72) Inventors: Diogo de Sousa Martins, Sao Paulo (BR); Pierre Roy, Paris (FR); Giovanni Cavallo, Rome (IT); Fulvio Foschini, Rome (IT)

(73) Assignee: KEMIN INDUSTRIES, INC., Des Moines, IA (US)

( * ) Notice: Subject to any disclaimer, the term of this patent is extended or adjusted under 35 U.S.C. 154(b) by 108 days.

This patent is subject to a terminal disclaimer.

(21) Appl. No.: 14/977,048

(22) Filed: Dec. 21, 2015

(65) Prior Publication Data

US 2016/0175148 A1 Jun. 23, 2016

Related U.S. Application Data

(60) Provisional application No. 62/094,663, filed on Dec. 19, 2014.

(51) Int. Cl.
| | |
|---|---|
| *A61F 9/00* | (2006.01) |
| *A61K 9/127* | (2006.01) |
| *A61K 31/045* | (2006.01) |
| *A61K 9/00* | (2006.01) |
| *A61K 31/047* | (2006.01) |
| *A61K 31/065* | (2006.01) |
| *A61P 27/00* | (2006.01) |
| *A61P 43/00* | (2006.01) |
| *A61N 1/30* | (2006.01) |
| *A61N 1/04* | (2006.01) |

(52) U.S. Cl.
CPC .......... *A61F 9/0026* (2013.01); *A61F 9/0008* (2013.01); *A61K 9/0009* (2013.01); *A61K 9/0051* (2013.01); *A61K 9/127* (2013.01); *A61K 31/045* (2013.01); *A61K 31/047* (2013.01); *A61K 31/065* (2013.01); *A61P 27/00* (2018.01); *A61P 43/00* (2018.01); *A61N 1/044* (2013.01); *A61N 1/303* (2013.01)

(58) Field of Classification Search
None
See application file for complete search history.

(56) References Cited

U.S. PATENT DOCUMENTS

| | | |
|---|---|---|
| 2003/0181531 A1 | 9/2003 | Sherris |
| 2005/0245856 A1* | 11/2005 | Roy .......................... A61F 9/00 604/20 |
| 2010/0034749 A1 | 2/2010 | Schulze et al. |
| 2010/0093648 A1 | 4/2010 | Cruz |
| 2012/0089077 A1 | 4/2012 | Roy |
| 2013/0178821 A1 | 7/2013 | Foschini et al. |
| 2013/0310732 A1 | 11/2013 | Foschini et al. |

OTHER PUBLICATIONS

Hanus et al, "Current therapeutic developments in atrophic age-related macular degeneration," The British Journal of Ophthalmology, vol. 100, No. 1, pp. 122-127 (2016). (Year: 2016).*
Meyers et al, "Genetic Evidence for Role of Carotenoids in Age-Related Macular Degeneration in the Carotenoids in Age-Related Eye Disease Study (CAREDS)," Investigative Ophthalmology & Visual Science, vol. 55, No. 1, pp. 587-599 (2014). (Year: 2014).*
Silvestri et al ("Is genetic predisposition an important risk factor in age-related macular degeneration?," Eye, vol. 8, No. 5, pp. 564-568 (1994). (Year: 1994).*
Mares-Perlman et al, "The Body of Evidence to Support a Protective Role for Lutein and Zeaxanthin in Delaying Chronic Disease. Overview," The Journal of Nutrition, vol. 132, No. 3, pp. 518S-524S (2002). (Year: 2002).*
Hsu, "Drug delivery methods for posterior segment disease," Current Opinion in Ophthalmology, vol. 18, No. 3, pp. 235-239 (2007). (Year: 2007).*
Shin et al., "Change of Retinal Nerve Fiber Layer Thickness in Various Retinal Diseases Treated With Multiple Intravitreal Antivascular Endothelial Growth Factor", Feb. 27, 2014, pp. 2403-2411, Publisher: The Association for Research in Vision and Ophthalmology, Inc.
Arboleda et al., "Evaluating In Vivo Delivery of Riboflavin With Coulomb-Controlled Iontophoresis for Corneal Collagen Cross-Linking: A Pilot Study", "The Association for Research in Vision and Ophthalmology, Inc", Jan. 1, 2014, pp. 2731-2738, Publisher: www.iovs.org.
Cohen et al., "Evaluation of Dexamethasone Phosphate Delivered by Ocular Iontophoresis for Treating Noninfectious Anterior Uveitis", "American Academy of Ophthalmology", Jan. 1, 2012, pp. 66-73, Publisher: Elsevier.
Patane et al., "Evaluation of Ocular and General Safety Following Repeated Dosing of Dexamethasone Phosphate Delivered by Transscleral Iontophoresis in Rabbits", Jan. 1, 2013, pp. 760-769, vol. 29, No. 8, Publisher: Journal of Ocular Pharmacology and Therapeutics.
Horwath-Winter et al., "Iodide iontophoresis as a treatment for dry eye syndrome", Jan. 1, 2005, pp. 40-44, Publisher: BJO.
Halhal et al., "Iontophoresis: from the lab to the bed side", "Experimental Eye Research", Jan. 1, 2004, pp. 751-757, vol. 78, Publisher: Elsevier.
Patane et al., "Ocular iontophoresis of EGP-437 (dexamethasone phosphate) in dry eye patients: results of a randomized clinical trial", "CLinical Ophthalmology", Jan. 1, 2011, pp. 633-635, vol. 5, Publisher: Dove Press.
Molokhia et al., "Transscleral iontophoretic and intravitreal delivery of a macromolecule: Study of ocular distribution in vivo and postmortem with MRI", "Exp eye Res", Oct. 10, 2009, pp. 418-425, vol. 88, No. 3, Publisher: NIH.

(Continued)

*Primary Examiner* — Dennis J Parad
(74) *Attorney, Agent, or Firm* — Nyemaster Goode P.C.

(57) ABSTRACT

Iontophoresis, a minimally-invasive methodology that uses a weak electric current to enhance penetration of ionized molecules into tissues, was found to be an effective technique for the intraocular delivery of large bioactive molecules, specifically lutein.

3 Claims, 2 Drawing Sheets

(56) References Cited

OTHER PUBLICATIONS

Aman et al. "Application of HPLC coupled with DAD, APcI-MS and NMR to the analysis of lutein and zeaxanthin stereoisomers in thermally processed vegetables," Journal of Food Chemistry, vol. 92, 2005, pp. 753-763.
Arnold et al. "Carotenoids and chlorophylls in process xanthophyll-rich food," LWT—Food Science and Technology, vol. 57, 2014, pp. 442-445.
Eljarrat-Binstock et al., "Methlprednisolone Delivery to the Back of the Eye Using Hydrogel Iontophoresis," Journal of Ocular Pharmacology and Therapeutics, Volume 24, No. 3, 2008, pp. 344-351.
Eljarrat-Binstock et al., "In Vitro and In Vivo Evaluation of Carboplatin Delivery to the Eye Using Hydrogel-Iontophoresis," Current Eye Research, vol. 33, 2008, pp. 269-275.
Eljarrat-Binstock et al., "Charged nanoparticles delivery to the eye using hydrogel iontophoresis," Journal of Controlled Release, vol. 126, 2008, pp. 156-161.
Eljarrat-Binstock et al., "Transcorneal and transscleral iontophoresis of dexamethasone phosphate using drug loaded hydrogel," Journal of Controlled Release, vol. 206, 2005, pp. 386-390.
Eljarrat-Binstock et al., "Iontophoresis: A non-invasive ocular drug delivery," Journal of Controlled Release, vol. 110, 2006, pp. 479-489.
Fratianni et al., "Degradation of careotenoids in orange juice during microwave heating," LWT—Food Science and Technology, vol. 43, 2010, pp. 867-871.
Frede et al., "Stability and cellular uptake of lutein-loaded emulsions," Journal of Functional Foods, vol. 8C, 2014, pp. 118-127.
Garcia-Parra et al., "Application of innovative technologies, moderate-intensity pulsed electric fields and high-pressure thermal treatment, to preserve and/or improve the bioactive compounds content of pumpkin," Innovative Food Science and Emerging Technologies, vol. 45, 2018, pp. 53-61.
Lim et al., "Preparation and characterization of a lutein loading nanoemulsion system for ophthalmic eye drops," Journal of Drug Delivery Science and Technology, vol. 36, 2016, pp. 168-174.
Ma et al., "Influence of technical processing units on the a-carotene, b-carotene and lutein contents of carrot (*Daucus carrot* L.) juice," Journal of Functional Foods, vol. 16, 2015, pp. 104-113.
McInerney et al., "Effects of high pressure processing on antioxidant activity, and total carotenoid content and availability, in vegetables," Journal of Innovative Food Science and Emerging Technologies, vol. 8, 2007, pp. 543-548.
Mitri et al., "Lipid nanocarriers for dermal delivery of lutein: Preparation, characterization, stability and performance," International Journal of Pharmaceutics, vol. 414, 2011, pp. 267-275.
Myles et al., "Recent progress in ocular drug delivery for posterior segment disease: Emphasis on transscleral iontophoresis," Advanced Drug Delivery Reviews, vol. 57, 2005, pp. 2063-2079.
Pescina et al., "In vitro trans-scleral iontophoresis of methylprednisolone hemisuccinate with short application time and high drug concentration," International Journal of Pharmaceutics, vol. 451, pp. 12-17.
Plaza et al., "Carotenoid and flavanone content during refrigerated storage of orange juice processed by high-pressure, pulsed electric fields and low pasteurization," LWT—Food Science and Technology, vol. 44, pp. 834-839.
Del Pozo-Rodriguez et al., "Lipid Nanoparticles as Drug/Gene Delivery Systems to the Retina," Journal of Ocular Pharmacology and Therapeutics, vol. 29, No. 2, 2013, pp. 173-188.
Provesi et al., "Changes in carotenoids during processing and storage of pumpkin puree," Journal of Food Chemistry, vol. 128, 2011, pp. 195-202.
Lin et al., "Stability of carotenoids in tomato juice during processing," European Food Research and Technology, vol. 221, 2005, pp. 274-280.
Tan et al., "Liposomes as Vehicles for Lutein: Preparation, Stability, Liposomal Membrane Dynamics, and Structure," Journal of Agricultural and Food Chemistry, vol. 61, 2013, pp. 8175-8184.
Tan et al., "Modulation of the carotenoid bioaccessibility through liposomal encapsulation," Calloids and Surfaces B: Biointerfaces, vol. 123, 2014, pp. 692-700.
Tan et al., "Liposomes as Delivery Systems for Carotenoids: Comparative Studies of Loading Ability, Storage Stability and in vitro Release," Journal of Food and Function, 34 pages.
Updike et al., "Thermal Processing of Vegetables Increases Cis Isomers of Lutein and Zeaxanthin," Journal of Agricultural and Food Chemistry, vol. 51, 2003, pp. 6184-6190.
Vollmer et al., "In Vivo Transscleral Iontophoresis of Amikacin to Rabbit Eyes," Journal of Ocular Pharmacology and Therapeutics, vol. 18, No. 6, 2002, 11 pages.
Xia et al., "Preparation of lutein proliposomes by supercritical anti-solvent technique," Food Hydrocolloids, vol. 26, 2012, pp. 456-463.

\* cited by examiner

INTRAOCULAR DELIVERY OF BIOACTIVE MOLECULES USING IONTOPHORESIS

This application claims priority to U.S. Patent Application Ser. No. 62/094,663, filed Dec. 19, 2014, which is incorporated herein in its entirety by this reference.

BACKGROUND OF THE INVENTION

The present invention relates generally to the use of bioactive molecules to ocular tissues and, more specifically, to the delivery of lutein to the macula using iontophoresis.

Lutein (and zeaxanthin) are associated with reducing the risk of developing AMD (Age-related Macular Degeneration) and cataract extraction due to its antioxidant and photoprotective effects, and its exclusive distribution in the eye macula[1]. Age is one of the most important risk factors for AMD, typically affecting individuals over 50 years old[2-4]. There are two types of AMD, 'dry AMD' and 'wet AMD'. Dry AMD develops when macular cells become damaged as a result of waste product accumulation called "drusen". It is the most common and least serious type of AMD. An estimated high number of those that present dry AMD symptoms will develop wet AMD, which develops when abnormal blood vessels from underneath the macula grow and lead to irreversible cell damage[2-4].

Lutein has been widely used through oral supplementation with the rationale that systemic circulation can bring lutein to the coroidal circulation for uptake into the macula, through xanthophyll-binding protein[5]. However, several reports demonstrate that only a small percentage of lutein reaches the macula[6-8]. Moreover, due to eye barrier limits, therapeutic treatments in the posterior eye segment are difficult. Since the eye is protected by the tear film, corneal, vitreous, blood-retinal and blood-aqueous barriers, it is very difficult to deliver drugs to the eye, particularly to the retina, in sufficient concentrations and with minimal side-effects[9,10]. In-situ applications have been used to overcome this problem; however, slow delivery systems, such as implants, are very invasive and expensive. Over the past few years, the results of many studies have highlighted the risks of these treatments[11,12].

Recently, intra-vitreous injections of lutein have been used to stain specific preretinal membranes and other eye structures during surgery[13-16]. This has been the first data on in-situ delivery of lutein towards the macula, exploiting lutein's intrinsic staining effect. Lutein's potential of delaying AMD progression and putative neuroprotective action shown in different trials has not yet been proven through in-situ application following intraocular delivery. Intravitreous injection of lutein for a prevention purpose may be too invasive as a strategy of delivering lutein to the macula, with the disadvantage of poor patient acceptance.

Ocular iontophoresis is a minimally invasive method used to propel by electrical force high concentrations of target molecules transsclerally or/and transcorneally. It uses a small electrical current applied to an iontophoretic chamber containing the molecule of interest and vehicle[17]. Several reports revealed that lutein, which is found in high concentrations in the macula of the human eye, has the potential of delaying AMD progression, in addition to potential neuroprotective action[18-20].

Here we report a novel way of delivering lutein to the retina, so its presence in the parafovea macular region can be enhanced significantly and thereby delay the progression of AMD and protect retinal endothelial cells. Different iontophoresis delivery systems for ophthalmic use have been created and have been used to safely and effectively deliver medication to both the anterior and posterior segments of the human eye[21]. With this technology, it is possible to deliver significant amounts of bioactive molecules, including macromolecules, across the cornea and sclera. In the work reported here, a lutein emulsion has been diffusively delivered to the macula by iontophoresis[22-23]. The idea was to develop a minimally invasive method of propelling high concentrations of charged lutein, transclerally or/and transcorneally by iontophoresis. We have assessed the distribution and concentration of lutein in the different ocular tissues using two-photon microscopy, Raman spectroscopy and HPLC after scleral and corneal iontophoretic application. The main advantage of this approach is to use of a medical device that is safer and easier to have patient compliance, avoiding the complications of frequent and high dose injections or surgical implantations. This procedure can be performed quickly in the doctor's office during a normal eye care appointment with no need of a surgical environment.

SUMMARY OF THE INVENTION

Iontophoresis, a minimally invasive methodology that uses a low electric current to enhance penetration of ionized compounds into tissues, was found to be effective for the intraocular delivery of lutein. Fourteen pigmented rabbits were treated by application onto the cornea and sclera of an iontophoretic reservoir filled with lutein emulsion with or without current (20.0 and 0.0 mA, respectively). After iontophoresis, the ocular tissues from both eyes (test and control) were collected and lutein delivery was assessed by visual comparison between treated eye and untreated contralateral eye. The transcorneal and transscleral iontophoresis application resulted in the delivery of lutein to the rabbit cornea in all treated eyes (time 0 h). The application of lutein also created an orange trace on the sclera limbus and a slight orange coloration in the eye conjunctiva, demonstrating the transport of the emulsion also to these tissues. In this work we have shown for the first time that iontophoresis is an effective technique for intraocular delivery of lutein.

In the present invention, lutein distribution in the eye after iontophoresis procedure was assessed to confirm that high quantities of lutein were delivered to the posterior retina by this technique. Results indicate that iontophoresis is an effective method of delivering a positively charged liposomal emulsion of lutein into rabbits eyes. Furthermore, experiments were performed using optimized formulations of lutein emulsion and an alternative iontophoretic prototype to evaluate lutein distribution in different eye tissues.

Trials were also performed with human cadaveric eyes to which a low electric current was applied to evaluate lutein delivery through the cornea and sclera. The cornea, sclera, choroid, peripheral and central retina from treated and non-treated eyes were collected and analyzed by two-photon microscopy in order to visualize the distribution of lutein-containing liposomes.

The transscleral iontophoretic application resulted in the delivery of the lutein mainly to the posterior retina region, revealing the pathway of lutein after the iontophoresis occurs via ciliary body/pars plana followed by passive diffusion until reaching the posterior retina. The absence of lutein in the choroid can be explained by the narrow size of tight junctions of the retinal pigmented epithelium, which impair the passage of the larger liposomal vesicles, thereby trapping lutein in the retina inner layers.

With this work we demonstrated for the first time the in situ delivery of lutein to the posterior eye segment through a novel, minimally invasive method. The results demonstrate that scleral iontophoresis of lutein is an effective strategy of delivering lutein to the macula, which represents an alternative to the current methods used to delay diseases in the posterior eye segment, such as AMD.

Iontophoresis has the advantage of being a minimally invasive method and, therefore, is safer than the alternative methods of intraocular delivery of compounds, namely implants and intra-ocular injections. Consequently, iontophoresis will have a higher patient compliance since it avoids the complications of a surgical implantation or frequent and high dose intravitreal injections. Another advantage is this technique is less expensive than those procedures and can be performed quickly in the doctor's office during a normal eye care appointment with no need for a surgery environment.

DETAILED DESCRIPTION OF PREFERRED EMBODIMENTS

Figure 1:
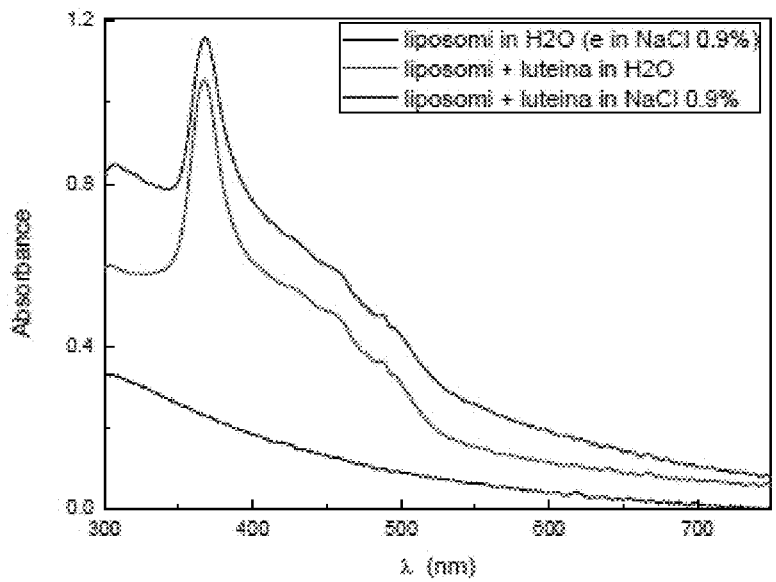
FIG. 1 is a chart of Lipo+ absorption spectra (300 to 750 nm), 1:50 dilution in 0.9% NaCl (blue) or distilled water (red); the control spectrum (liposome solution without lutein) is represented.

The terms "administration of" or "administering a" compound should be understood to mean providing a compound of the invention to the individual in need of treatment in a form that can be introduced into that individual's body in a therapeutically useful form and therapeutically effective amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The term "effective amount" as used herein refers to the amount necessary to elicit the desired biological response. As will be appreciated by those of ordinary skill in this art, the effective amount of a composite or bioactive agent may vary depending on such factors as the desired biological endpoint, the bioactive agent to be delivered, the composition of the encapsulating matrix, the target tissue, etc.

As used herein, the term "extract" refers to a product prepared by extraction. The extract may be in the form of a solution in a solvent, or the extract may be a concentrate or essence which is free of, or substantially free of solvent. The term extract may be a single extract obtained from a particular extraction step or series of extraction steps or the extract also may be a combination of extracts obtained from separate extraction steps. For example, extract "a" may be obtained by extracting cranberry with alcohol in water, while extract "b" may be obtained by super critical carbon dioxide extraction of cranberry. Extracts a and b may then be combined to form extract "c". Such combined extracts are thus also encompassed by the term "extract".

As used herein, the term "fraction" means the extract comprising a specific group of chemical compounds characterized by certain physical, chemical properties or physical or chemical properties.

The term "preventing", when used in relation to a condition, such as cancer, an infectious disease, or other medical disease or condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population.

By "pharmaceutically acceptable" it is meant the carrier, diluent or excipient must be compatible with the other ingredients of the formulation and not deleterious to the recipient thereof.

The term "synergistic" is well understood in the art and refers to two or more components working together so that the total effect is greater than the sum of the components.

The term "treating" is well understood in the art and refers to curing as well as ameliorating at least one symptom of any condition or disorder.

The term "prophylactic or therapeutic" treatment is well understood in the art and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The compounds of this invention may be administered to subjects (humans and animals, including companion animals, such as dogs, cats and horses) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

Example 1—Intra-Ocular Delivery of Lutein in Rabbit Eyes

Materials and Methods

Formulation Work.

Among the different delivery systems currently used to improve the stability of compounds, liposomes have advantages due to their biocompatibility, sustained release potential, and the ability to carry both hydrophobic and hydrophilic compounds[16]. In this work, crystalline lutein (Kemin Foods, FloraGLO® Crystalline Lutein lot. 1401103302) was encapsulated in liposomes using phospholipids 90H (Lipoid GmbH, lot 529400-2120046-12-112, CAS 308068-11-3) and octadecylamine (Sigma-Aldrich lot BCBK6340V, CAS 124-30-1). Lipid film was prepared using 90H phospholipids, octadecylamine and lutein dissolved in $CHCl_3$/MeOH (2:1) (Sigma-Aldrich, lot SHBC4982V, CAS 67-66-3/Sigma-Aldrich, lot SZBC237BV, CAS 67-56-1). Solvents were removed under vacuum by rotary evaporation; the solution was dried under vacuum at 40° C. by a Heidolph rotavapor, the speed of the rotavapor was modulated in order to reduce bubble formation and splashing that could cause loss of product and a dry thin film was obtained after 1-2 hours. To remove any trace of solvents, the thin film was left under vacuum for at least 16 hours at room temperature. Lipid film hydration was performed by adding distilled water (Water Ultrapure—MilliQ-by AquaMax—conductivity 0.054 uS/cm) at 40-45° C. to the lipid film to hydrate lipids and form large liposome vesicles. The homogenization of the large liposome vesicles was achieved using Ika Works ULTRA-TURRAX T 25 Digital Homogenizer (Staufen, Germany), and reduction of liposome vesicles to a nano size range has been performed by extrusion using large-scale Microfluidizer® high fluid processor M-110EH at 50-60° C. and 1200 bar. This process was repeated 5 times. Sterilization of the emulsion was performed at 121° C. for 20 minutes at 1 atm. Table 1 shows liposome emulsion composition. Size distribution, zeta potential, osmolality and pH of the final product were analyzed after sterilization and are summarized in Table 2.

TABLE 1

Lutein liposome emulsion composition.

| Composition | % w/w |
|---|---|
| 90H phospholipids | 1.000 |
| Octadecylamine | 0.005 |
| Lutein crystals | 0.050 |
| Distilled water to | 100 g |

TABLE 2

Liposome characteristics after sterilization.

| pH | Osmolality (mOsM/kg) | Mean diameter (nm) | Zeta potential (mV) |
|---|---|---|---|
| 6.84 | 15 | 194 | +36.93 |

Ocular Iontophoresis Device.

The iontophoresis device consisted of two disposable components: an ocular applicator and a return electrode. These two components were connected to a reusable generator. The ocular applicator was composed by a polycarbonate reservoir (diameter 9 mm, height 4.5 mm, volume 0.5 ml) and a stainless steel electrode (AISI 304) connected with a lead to the generator (anode-positive electrode). The return electrode was a 25G intradermic needle, inserted in the neck (front side) and connected with a crocodile clip and lead to the generator (cathode). The generator (EYEGATE CCI Generator 6121-EYE, Eyegate Pharma, Paris France) was a constant current type, setting range 0.25 mA-2.5 mA (10 increments of 0.25 mA) for the current and 0.5 min-5 min for the time (10 increments of 0.5 min) The resulting voltage applied was measured during the study with a multimeter.

Animals.

Fourteen pigmented rabbits strain HY79b (Breeder: "HYP-HARM"—FR-49450 ROUSSAY) were used in this study. All animals were identified individually using an ear tag and using a marker in the ears following the inclusion examination. Animals were held in observation for 3 days following their arrival, and were daily observed for signs of illness with particular attention to the eyes. Animals were individually housed in standard cages, under identical environmental conditions. The temperature was held at 15-21° C. and the relative humidity at 55±10%. Rooms were continuously ventilated (≥15 air volumes per hour). Temperature and relative humidity were continuously controlled and recorded. Animals were routinely exposed (in-cage) to a 10-200 1× light in a 12-hour light (from 7:00 a.m. to 7:00 p.m.) and 12-hour darkness controlled cycle. Throughout the study, animals had free access to food and water. They were fed a standard dry pellet diet (150 g/day), LASQCdiet® Rab-14H (LASVENDI GMBH, Soest Germany). Tap water, regularly analysed, was available ad libitum from plastic bottles. All standard operating procedures and protocols described in this study plan have been reviewed by a certified Ethical Committee. All animals were treated according to the Directive 2010/63/UE European Convention for the Protection of Vertebrate Animals used for Experimental[17] and Other Scientific Purposes and to the Association for Research in Vision and Ophthalmology (ARVO) Statement for the Use of Animals in Ophthalmic and Vision Research[18].

Experimental Procedure.

Fourteen pigmented rabbits from HY79b strain were randomly divided into two groups: control (passive application: without electric current; animals #9-14) and test group (iontophorectic application: with electric current; animals #1-8). These two groups were subdivided in two time-points (0 and 2 hours). Table 3 summarizes the study design.

TABLE 3

Study design.

| Group No. | Drug | Administration | Time-points | Animals id# |
|---|---|---|---|---|
| 1 | Lutein emulsion | Iontophoretic delivery | 0 h | 1, 2, 3, 4 |
| 2 | | (charge = 20.0 mA) | 2 h | 5, 6, 7, 8 |
| 3 | | Iontophoretic delivery | 0 h | 9, 10, 11 |
| 4 | | (charge = 0.0 mA) | 2 h | 12, 13, 14 |

Lutein emulsion was administered by iontophoresis to anesthetized animals (intra muscular injection of a mix xylazine/ketamine), aided with a blepharostat and under local anesthesia (one drop of Cebesine®: 0.4% oxybuprocaine, Thea, lot F6757) about 10 min before application). Animals were treated by application onto the cornea and sclera of a 9-mm iontophoretic applicator filled with lutein for 10 minutes on right eye. A charge of 0.0 mA or 20.0 mA was applied on each eye, depending on the group (see Table 3). The iontophoretic applicator was impregnated with 0.5 mL of lutein liposome emulsion just before dosing; the electrode of the device was covered with lutein emulsion. All administrations were followed by balanced salt solution (BSS) washing.

Immediately after the iontophoretic application of the right eye or 2 hours post-application (see Table 3), animals were euthanized by intravenous administration of overdosed pentobarbital, which is among the recommended methods by the European Authorities[17]. Cornea (C), aqueous humor (AH), ciliary-body (CB), retina (R), vitreous (V) and sclera (SC) from both eyes were sampled and weighed. A visual evaluation of the coloration of the samples was performed before storing them at −80° C. for future HPLC (high-performance liquid chromatography) analysis.

Results

Ocular Iontophoretic Delivery of Lutein Emulsion in Pigmented Rabbits.

In order to evaluate the capacity of lutein to be delivered by iontophoresis, we produced liposomes carrying lutein (positively charged) and applied this emulsion for 10 min with 2.0 mA into the cornea/sclera of pigmented rabbits. The efficacy of delivery by iontophoresis was evaluated by visual assessment of the collected tissues. Table 4 summarizes the results after the application of lutein emulsion, with and without current.

Discussion

Approximately 10% of people over 65 years around the world suffer from AMD disease[19]. Different trials have indicated lutein is a potential AMD progression delayer and also a potential neuroprotective molecule[13, 20-22]. Moreover, lutein is a natural component of the eye, with intrinsic macular tropism, being specifically deposited in the para-foveal area where it is congenital[1]. These features can be an advantage towards the current products used to control AMD. The available treatments for this pathology involve intraocular injections that have side effects, are troublesome to the patient and expensive, so the development of a more safe and effective treatment is crucial. Over the past few years, results of many studies have highlighted the risks of intravitreal injections. The need for frequent administration of drugs through intravitreal injections can lead to retinal detachment, endophthalmitis and increased intraocular pressure. Both noninfectious and infectious inflammation has been reported as complications of intravitreal injections. With the increasing rates of intravitreal injections since their approval for use, the incidence of infectious endophthalmitis has been extensively studied[23, 24]. In this work we tested, for the first time a minimally invasive technology to deliver lutein in-situ. Iontophoresis has the advantage of being a minimally invasive method and therefore is safer and easier to improve patient compliance, since it avoids the complications of a surgical implantation or frequent and high dose

TABLE 4

Coloration after iontophoretic application.

| Rabbit ID# | Iontophoresis | Tissue collection time-point | Ocular tissue coloration (upon sampling) | |
|---|---|---|---|---|
| | | | Untreated eye (left) | Treated eye (right) |
| 1 | 2.0 mA charge for 10 min | 0 h | No coloration | Cornea: slight circular orange trace |
| 2 | | | No coloration | Cornea: circular orange trace. SC: orange trace on the limbus. CJ: slight orange coloration |
| 3 | | | No coloration | Cornea: circular orange trace. SC: orange trace on the limbus. CJ: slight orange coloration |
| 4 | | | No coloration | Cornea: circular orange trace |
| 5 | | 2 h | No coloration | Cornea: circular orange trace |
| 6 | | | No coloration | No coloration |
| 7 | | | No coloration | No coloration |
| 8 | | | No coloration | Cornea: circular orange trace |
| 9 | 10 min application without charge | 0 h | No coloration | No coloration |
| 10 | | | No coloration | No coloration |
| 11 | | | No coloration | No coloration |
| 12 | | 2 h | No coloration | No coloration |
| 13 | | | No coloration | No coloration |
| 14 | | | No coloration | No coloration |

Note:
C = Cornea;
SC = Sclera;
CJ = Conjunctiva

Subsequently to the iontophoresis application, all the eyes treated with 20.0 mA of current (time 0 h) revealed a circular orange color in the cornea revealing the present of lutein emulsion in the tissues. The application of lutein also originated in two eyes (#2 and #3) an orange trace on the sclera limbus and a slight orange coloration in the eye conjunctiva. After 2 h of treatment only half of the treated eyes showed this coloration in the cornea (#5 and #8), this event may indicate that subsequently to the application, the emulsion diffuses into the eye. No delivery into the different ocular tissues was observed without current.

of intravitreal injections[12]. In fact different pre-clinical and clinical studies reported the safety of repeated ocular iontophoresis applications[14, 25, 26]. Another advantage is this method is less expensive and can be performed quickly in the doctor's office during a normal eye care appointment with no need for a surgery environment. Different studies established the use of iontophoresis for the treatment of human eye diseases, for instance in management of active corneal graft rejection[27], treatment of dry eye disease[14, 28], noninfectious anterior uveitis[15] and keratoconus disease[29].

In this investigation we have used iontophoresis that involves the application of a weak direct current during 10 minutes that drives charged molecules across the eye tissues. The iontophoretic application resulted in the penetration of the emulsion of liposomes carrying lutein (ionized drug) through the corneal segment of the eye.

This study is an effective proof-of-concept that clearly shows an intraocular delivery of lutein emulsion through iontophoresis technique.

Example 2—Intra-Ocular Delivery of Lutein in Cadaveric Eyes

Materials and Methods

Formulation Work.

It has been demonstrated that positive particles are better candidates for iontophoretic application as drug carrier than the negatively charged particles due to higher penetration into ocular tissues[38]. Furthermore, the electrical field forces the positive charged molecules to move into eye membranes (negatively charged)[39]. In this work we took advantage of the fact that the membranes present in the human eye, at physiological pH, are negatively charged and for developing a positively charged emulsion carrying lutein to be delivered through iontophoresis application. Due to the fact that lutein is a molecule with a large molecular weight, lipophilic and insoluble in water, the delivery of this carotenoid trough iontophoresis without modifications is nearly impossible[1]. In order to overcome that, a formulation with positively charged liposome vesicles that behave as carriers of lutein molecules was prepared (Lipo+). The lipid film was prepared using phospholipon 90H (Lipoid GmbH, lot 529400-2120046-12-112, CAS 308068-11-3), octadecylamine (Sigma-Aldrich lot BCBK6340V, CAS 124-30-1) crystalline lutein (Kemin Health, FloraGLO® Crystalline Lutein lot. 1401103302). For preparation of 4-5 L, the compounds were dissolved in 500-800 mL of CHCl$_3$/MeOH (1:1 v/v) (Sigma-Aldrich, lot SHBC4982V, CAS 67-66-3/Sigma-Aldrich, lot SZBC237BV, CAS 67-56-1) by heating at 30-35° C. Please see formulation composition in Table 5. Solvents were removed under vacuum by rotary evaporation; the solution was dried under vacuum at 40° C. by a Heidolph rotavapor, and a dry thin film was obtained after 1-2 hours. The thin film was left under vacuum for at least 16 hours at room temperature to ensure the complete removal of any trace of solvents. The content of organic solvents was analyzed by gas chromatography (GC) and was assured to be less than 25 ppm. Lipid film hydration was performed by adding distilled water (Water Ultrapure—MilliQ-by Aqua-Max—conductivity 0.054 uS/cm) at 65° C. to the lipid film to form large liposome vesicles. Homogenization of these large liposomes vesicles was achieved using Ika Works ULTRA-TURRAX T 25 Digital homogenizer (Staufen, Germany) at 2000-4000 rpm and reduction of liposome vesicles to nano size range has been performed by extrusion using large-scale Microfluidizer® high fluid processor M-110 EH at 50-60° C. and 1200 bar. This process was repeated 5 times. Sterilization of the emulsion was performed at 121° C. for 20 minutes at 1 atm. After the sterilization process, the characteristics of the liposomal formulation were recorded: pH (using a Mettler Toledo S20 instrument), osmolality (using Osmomat 3000), particle size and zeta potential (using dynamic light scattering (DLS), also known as photon correlation spectroscopy technique—Nicomp 380 DLS.

TABLE 5

Lutein liposome emulsion composition.

| Composition | % w/w |
| --- | --- |
| 90H phospholipids | 2.000 |
| Octadecylamine | 0.007 |
| Lutein crystals | 0.100 |
| Distilled water to | 100 g |

Spectrophotometric Evaluation of the Formulation.

Spectrophotometry was used to measure the absorbance and fluorescence properties of the Lipo+ solution (1:50 dilution in water or 0.9% NaCl). A solution including only liposomes (without lutein) was used as control. The absorbance spectra were traced between 300 and 750 nm for each sample and the fluorescence spectra between 480 and 650 nm, with excitation at 370 nm (chosen from the absorbance spectra results).

Particle Size and Zeta-Potencial.

Dynamic light scattering was used to evaluate the distribution of sizes of the components in the Lipo+ solution. Electrophoresis was performed to evaluate the zeta potential of the solution.

Ocular Iontophoretic Device.

The principle of ocular iontophoresis is applying an electric field to an electrolytic substance containing at least one product, in order to transport the product into the body or the organ to be treated, via the biological membranes of the eye[12].

A typical iontophoretic setting is made of two components: ocular applicator and a return electrode both connected to a generator. In this experiment, the ocular applicator comprised 2 electrodes to address independently corneal and scleral tissues. The ocular applicator (OPIA Technologies SAS, Paris, France) is made of polyurethane resin and comprises 2 reservoirs: central circular reservoir (diameter 8 mm, height 4.5 mm, volume 1 ml) and a stainless steel electrode, applied on the cornea surrounded by an annular reservoir (inner diameter 12.5 mm, outer diameter 18 mm height 4.5 mm, volume 1 ml) and a stainless steel electrode, applied on the sclera (pars plana region around the limbus). Each stainless steel electrode connected with a lead to a different constant current generator (anode-positive electrode). The return electrodes were assigned to each generator and respectively attached to the optic nerve (for the corneal electrode) and the equator region of the sclera (for scleral electrode), closing each electrical circuit independently. The generators (IONO-25, lacer Srl, Italy) were a constant current type, setting range 0.25 mA-2.5 mA (5 increments of 0.5 mA) for the current and time adjusted automatically to deliver a total dose of 20 mA·min. The resulting voltage applied was measured during the study for each circuit with 2 multimeters.

Cadaveric Eyes.

Six human cadaveric eye globes, from different healthy donors, were obtained from the Veneto Eye Bank Foundation (Venezia Zelarino, Italy). The human eyes were used in compliance with the guidelines of the Declaration of Helsinki for research involving the use of human tissue and were explanted between 3 and 16 hours after death and immediately preserved at 4° C. in corneal storage medium enriched with 6% dextran. The mean donor age was 63.6±5.9 years. The mean endothelial cell density was 2125±389 cells/mm$^2$. Each eye globe, submerged in dextran enriched solution, was shipped to the laboratory within 5 days. Four eye globes underwent corneo-scleral iontophoresis to deliver 0.1% lutein ophthalmic solution into the retinal tissue. Two eye globes were used as control: iontophoresis was performed without presence of the formulation.

Preparation of the Eyes.

Each eye globe was gently mounted into a specially designed holder, facing upward. The scleral and corneal passive electrodes were applied in the optic nerve and sclera, respectively. The eye was connected to a column manometer by a tube, filled with 0.9% sodium chloride solution, in order to maintain the pressure inside the eye at 15 mmHg during the experiment. The eye globe was first subjected to three cycles of pre-conditioning between 15 and 42 mmHg in order to stabilize the ocular tissues and mechanics during experiment. This preconditioning ensured to attain a unique reference state at the beginning of each experiment and to restore the corneal and scleral thickness to physiological levels. After pre-conditioning, the central corneal thickness (CCT) was measured, using an ultrasound corneal pachymeter (Pachmate, DGH, Exton, USA). In these samples, the mean CCT was 558±19 µm.

Impregnation with the Solution.

The active electrode (cathode), in a plastic bath, was applied to the corneal and scleral surface. The plastic tube was filled with foam, which was soaked with Lipo+ for 20 minutes. After this pre-soaking treatment, the tube was gently applied to the anterior surface of the eye globe and again filled with 2 mL of Lipo+ solution. The current density was set at 2.5 mA and delivered for 5 minutes for both generators connected to the cornea and sclera. After corneo-scleral iontophoresis, the eye globe was maintained, facing upward, in the eye holder with the pressure inside the eye at 15 mmHg for 80 minutes. This period allowed the lutein, which reached the retina by trans-scleral iontophoresis, to diffuse passively, through the retinal tissue, towards the macula, specially the para-foveal region. Two of the 6 eyes used in this study were used as control, thus no impregnation with the formulation was performed.

Tissue Evaluation.

After 80 minutes, the retinal tissue was isolated without inducing gross damage that could compromise their use for high-resolution two-photon imaging. Dissection of retinal, choroidal, corneal and scleral tissues was done using a standardized protocol[47]. Two-photon microscopy was used to evaluate penetration of lutein in the macular region of the retina. Before starting image acquisition on ocular tissues, several stacks on Lipo+ solution (0.005%, 0.002% and 0.001% dilutions in 0.9% sodium chloride) were acquired in order to understand the best filter to apply and enhance the two-photon fluorescence (TPF) signal emitted by lutein. The filter 550/80 nm (Semrock) was the most appropriate for the study of lutein (based in spectrophotometric studies) however, the filter 525/20 nm (Semrock) was found to give good results in terms of Signal-to-noise ratio (SNR). Therefore, the excitation used for ocular tissues evaluation was 835 nm and TPF light emitted by ocular tissue components was collected in backward direction by a non-descanned detector (NDD1) for reflected light reflection.

Resonance Raman Spectroscopy:

Resonant Raman scattering was used for evaluating the efficacy of iontophoresis delivery of lutein to the human retina in cadaveric eyes. A single-mode laser source (50 mW power), centered at 473.5 nm wavelength, was used as excitation source to perform resonance raman spectroscopy measurement. The laser beam was focused on the ocular tissues by a combination of lenses and a microscope objective (NA=0.25), so that the irradiated retina area was 1 mm in diameter; the laser power was reduced to 1 mW at the retinal plane using a neutral density filter. The Raman scattered light was collected by a photomultiplier tube (PMT), with spectral resolution of 10 $cm^{-1}$ and with an average of 80 dark counts rate. Raman signal intensity was recorded as photon counts per second (cps). Measurements were performed on three retinal regions: the inner sclera at the site of iontophoretic delivery (i.e., the perilimbal sclera facing towards the ciliary body); the retinal mid-periphery, which included the region of the retina surrounding the vascular arcades and the optic nerve head; and the macula. Measurements were performed in four areas across each region in order to collect enough data to correctly estimate data in the study and control eyes. Before the experiment, in order to find a correlation between the Raman readings and the actual lutein content of the ocular tissues, calibration experiments using thin quartz cuvettes filled with different concentration of lutein were performed.

Results

Lipo+ Spectral Characteristics.

Figure 2:
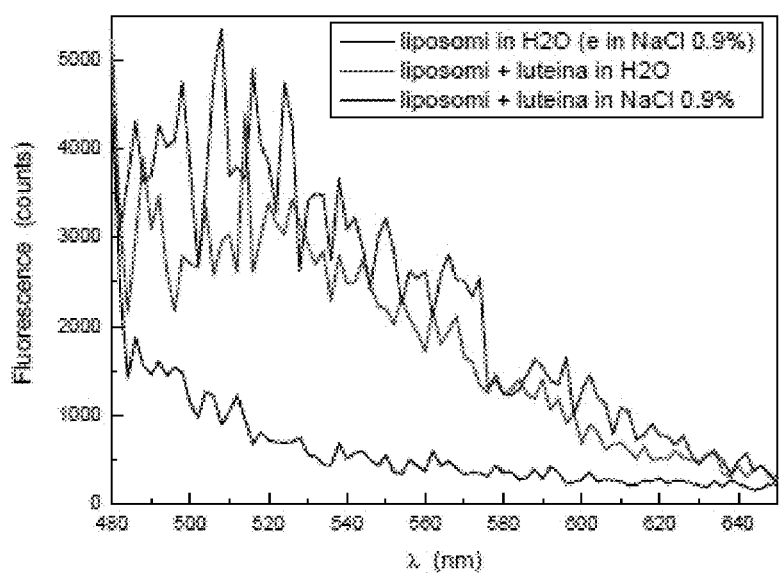
FIG. 2 is a chart of Lipo+ fluorescence spectra (480 to 650 nm), 1:50 dilution in 0.9% NaCl (blue) or distilled water (red); the control spectrum (liposome solution without lutein) is represented.

Absorbance and fluorescence spectra of Lipo+ solution were initially addressed in this study in order to determine the two-photon excitation wavelength. The absorption spectra were traced between 300 and 750 nm and are represented in FIG. 1. The Lipo+ solution showed an absorption peak at 370 nm and this was used as excitation wavelength to trace Lipo+ fluorescence spectra between 480 and 650 nm (FIG. 2). Lipo+ showed two fluorescent band peaks: 500-530 nm and 540-570 nm. Based on these results, the filter chosen for the two-photon experiments was the 550/88.

Lipo+ Physical Characteristics.

Figure 3:
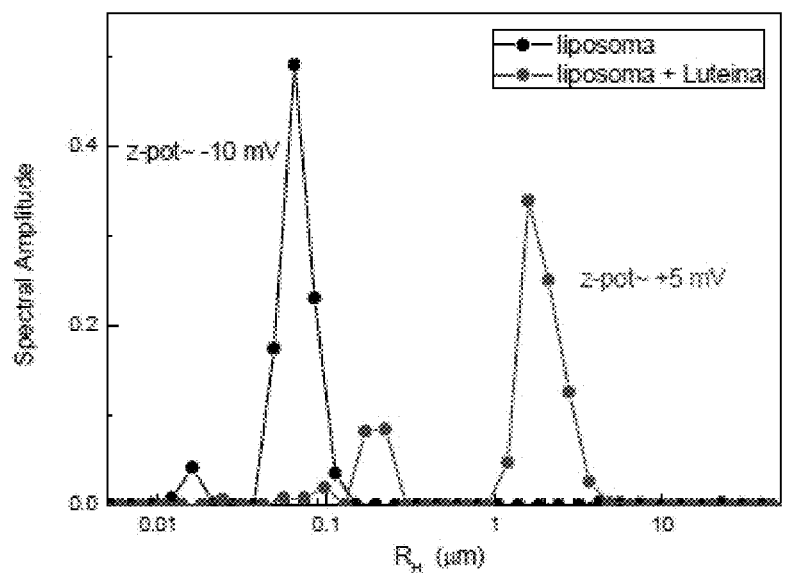
FIG. 3 is a chart of the dynamic light scattering and electrophoretic mobility to estimate particle size distribution and charge of Lipo+ solution: a 1:50 dilution in distilled water (red) was tested and also 1:50 liposome dilution in water (without lutein) as control.

Particle size and zeta-potential were also determined before iontophoresis testing, in order to confirm Lipo+ positive charge and size. These determinations were performed through dynamic light scattering and electrophoresis, respectively, for a 1:50 Lipo+ dilution in distilled water, and were also compared to the lutein-free liposome solution (as control). According to FIG. 3, Lipo+ aggregates peak at 3.5 µm (in average) and a smaller peak is also seen at 300 nm (in average), indicative of the individual liposomes. Also, the zeta potential determination showed a +5 mV charge for the Lipo+ solution.

Lutein Distribution in Cadaveric Eyes after Iontophoretic Application.

Although the filter chosen for the two-photon experiments was the 550/88 (based on previous fluorescence experiments), initial analysis of the lutein liposomal formulation revealed that the 525/20 filter gave better results in terms of SNR. In this initial calibration (with 0.005, 0.002 and 0.001% Lipo+ dilutions in 0.9% NaCl), liposomes were observed as spherical vesicles and the microscope was calibrated correctly (data not shown). This is a very important control because the retinal pigment cells are full of melanin, a pigment that excites at the same wavelength as lutein. Moreover, with this control we are able to distinguish between the lutein liposomes and the pigment.

In order to assess the distribution of the liposomes carrying lutein in human eye after iontophoretic application, five cadaveric eyes were exposed to a current of 2.5 mA for 5 min into the cornea/sclera, allowed to rest for 80 min (controlled intraocular pressure at 15 mmHg) and the different structures of the eye were collected: cornea, sclera, choroid, peripheral and central retina. The distribution of the liposomes was evaluated by two-photon microscopy (excitation at 835 nm). A sixth cadaveric eye was used as control: the eye was never in contact with the liposomal formulation.

In this, no liposomes were detected when the 835 nm laser was on, indicating that the signal is specific to exogenous lutein (data not shown).

Analysis of the different eye tissues collected showed that after combined corneo-scleral iontophoresis, lutein was abundant in the retina, while no lutein-enriched liposomes were found in the choroidal tissues for all tested eyes with the formulation.

Also, from the retinal investigation, Lipo+ solution was not able to cross the wall of retinal vessels, since liposomes were only found in the tissue surrounding the vessels.

For the anterior segment determinations (sclera and cornea), no lutein-enriched liposomes were found, neither in the corneal stroma nor in the sclera tissue, but were found in corneal epithelial cells In the retina it was also possible to observe more lutein in the outer part close to the photoreceptors than in the ganglion cells, the inner part of the retina.

Figure 4:
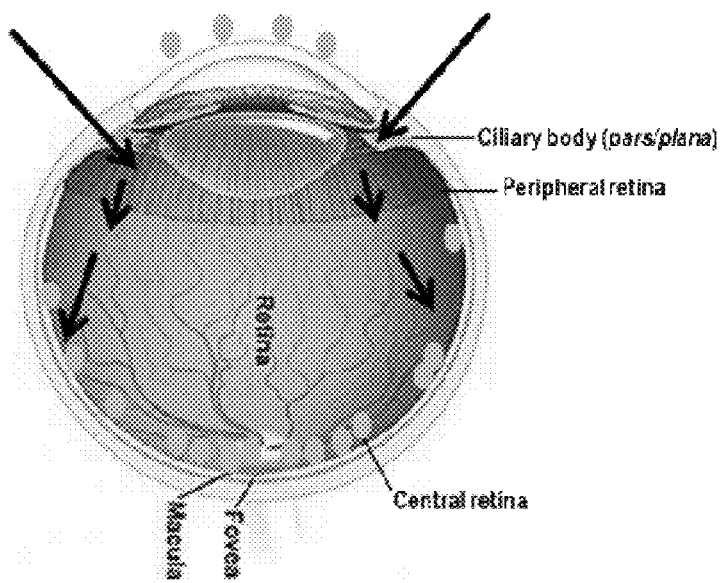
FIG. 4 is a schematic representation of lutein trajectory after iontophoresis application; scleral application deposits lutein to the back of the eye, whereas corneal application leaves lutein sitting on top of the corneal epithelial cells (orange spots); arrows indicate the entrance of lutein following iontophoresis application.

Since the choroid analysis revealed no liposomes were present in this region after the current application, these results indicate that after transscleral application of lutein by iontophoresis via ciliary body/pars plana, lutein liposomes diffuse passively through the eye membranes until reaching the posterior retina near the fovea. FIG. 4 shows a schematic representation of the lutein pathway within the eye. Analysis of corneal tissue following corneal iontophoresis application, revealed the liposomes were sitting on top of the epithelial cells of this tissue.

Resonance Raman spectroscopy analysis of different eye tissues was also performed. Raman signals were superimposed on a fluorescence background likely originating from intrinsic carotenoid fluorescein and lipofuscin fluorescence. To obtain an accurate reading of the Raman peak heights, free of background signals, we subtracted the influence of potentially overlapping noise spikes in the spectrum by polynomial fitting (up to 5th order) of the measured Raman line shapes for each measured spectrum. The final peak height of the C=C double bond signal at 1530 cm−1 was chosen as a signature of the presence of lutein.

In the inner sclera, the Raman peak at 1530 cm−1 measured in a treated eye was 7 times greater than control eye, providing the evidence of efficacy of iontophoresis in delivering lutein to the eye through the intact sclera. In the retinal mid-periphery, the Raman peak at 1530 cm−1 measured in a treated eye was 1.7 times greater than control eye, which indicated that a large amount of lutein reached the posterior pole of the retina at the end of iontophoresis treatment. In the macula, the Raman peak at 1530 cm−1 measured in a treated eye was 1.3 times greater than in controls, demonstrating that iontophoresis was effective in delivering lutein in the macula.

Discussion

Age-related macular degeneration (AMD) is the leading cause of irreversible blindness in people over 50 years in the developed world[40, 41]. More than 8 million Americans have AMD, and the overall prevalence of the disease is projected to increase by more than 50% by the year 2020[37]. Several epidemiological studies highlighted that lutein supplementation lead to an increase in the macular pigment optical density (MPOD) levels in early-stage AMD patients, being associated with protection from macular disease[42, 21]. In fact, lutein is naturally concentrated in the retina, where together with zeaxanthin forms the macular pigment. Acting as a blue light filter, lutein can protect the underlying photoreceptors in the center of the macula from photochemical damage[43]. The anti-oxidant properties of lutein may also protect the macula from oxidative stress[44].

The available solutions to slow AMD progression are based on intraocular injections or surgeries, encompassing evidenced side effects and possible complications such as retinal detachment, increased intraocular pressure and also noninfectious and infectious inflammation[23,33]. In this work, we used a minimally invasive in situ delivery of lutein to the posterior segment of the human eye. Iontophoresis has the advantage to be safer and easier method to have patient compliance and propelling high concentrations of a product of interest through the different eye layers until it reaches the retina. Different reports have established the safety of repeated treatments using ocular iontophoresis for the treatment of different diseases such as dry eye, noninfectious uveitis and keratoconus[14, 15, 25, 26, 28, 29].

Herein, using cadaveric eyes as pre-clinical model we applied a weak electric current to propel lutein into the eye, without side effects. We observed that lutein liposomes are mainly deposited in the peripheral and central retina near the fovea, but were absent from the choroidal regions. With this observation it is possible to extrapolate the pathway of lutein after a transscleral application is via ciliary body/pars plana, followed by passive diffusion through the ocular membranes until reaching the posterior retina region (FIG. 4). We proved for the first time that transscleral iontophoresis is an effective way of bringing lutein to the retina of the human eye providing a new way of fortifying the macular pigment. Upon deposition in the posterior region, it is postulated that lutein is able to reach the outer part of the retina where the photoreceptors are present, by passive diffusion/protein gradient. It can be argued the reason why lutein was not observed in the choroid is due to the neural retinal barrier which mesh size is 80-90 nm[45] (liposomes are 341 nm in size and can sometime form clusters of 2-3 μm, suggesting that lutein liposomes stay trapped in the retina (FIG. 4). Importantly, resonance Raman spectroscopy analysis revealed that lutein concentration is increased in the macula after iontophoresis. This observation clearly demonstrates that transscleral iontophoresis is an efficacious method of lutein delivery to the macula and is a valid alternative to the current methods for preventing the onset of AMD, prevent its progression and/or treat established disease.

After corneal iontophoresis application no liposomes were present in the corneal stroma. This fact can be explained since lutein is hydrophobic and the stroma is 70% composed of water, so very hydrophilic[46], which makes impossible for lutein to penetrate in this tissue.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

REFERENCES

1. Kijlstra A., Tian Y., Kelly E. R., Berendschot T. T. 2012. Lutein: more than just a filter for blue light. Frog Retin Eye Res. 31:303-315.
2. Yemelyanov A. Y., Katz N. B., Bernstein P. S. 2001. Ligand-binding characterization of xanthophyll carotenoids to solubilized membrane proteins derived from human retina. Exp Eye Res. 72:381-392.
3. Bone R. A., Landrum J. T., Guerra L. H., Ruiz C. A. 2003. Lutein and zeaxanthin dietary supplements raise macular pigment density and serum concentrations of these carotenoids in humans. J Nutr. 133:992-998.
4. Landrum J. T., Bone R. A., Joa H., Kilburn M. D., Moore L. L., Sprague K. E. 1997. A one year study of the macular pigment: the effect of 140 days of a lutein supplement. Exp Eye Res. 65:57-62.
5. Ma L., Lin X. M. 2010. Effects of lutein and zeaxanthin on aspects of eye health. J Sci Food Agric. 90:2-12.
6. Barar J., Javadzadeh A. R., Omidi Y. 2008. Ocular novel drug delivery: impacts of membranes and barriers. Expert Opin Drug Deliv. 5:567-581.
7. de la Fuente M., Ravina M., Paolicelli P., Sanchez A., Seijo B., Alonso M. J. 2010. Chitosan-based nanostructures: a delivery platform for ocular therapeutics. Adv Drug Deliv Rev. 62:100-117.
8. Sousa-Martins D., Maia M., Moraes M., Lima-Filho A. A., Rodrigues E. B., Chen J., Farah M. E., Santos L. B., Belfort R., Jr. 2012. Use of lutein and zeaxanthin alone or combined with Brilliant Blue to identify intraocular structures intraoperatively. Retina. 32:1328-1336.
9. Rodrigues E. B., Costa E. F., Penha F. M., Melo G. B., Bottos J., Dib E., Furlani B., Lima V. C., Maia M., Meyer C. H., Hofling-Lima A. L., Farah M. E. 2009. The use of vital dyes in ocular surgery. Surv Ophthalmol. 54:576-617.
10. Maia M., Furlani B. A., Souza-Lima A. A., Martins D. S., Navarro R. M., Belfort R., Jr. 2014. Lutein: a new dye for chromovitrectomy. Retina. 34:262-272.
11. Badaro E., Furlani B., Prazeres J., Maia M., Lima A. A., Souza-Martins D., Muccioli C., Lucatto L. F., Belfort R., Jr. 2014. Soluble lutein in combination with brilliant blue as a new dye for chromovitrectomy. Graefes Arch Clin Exp Ophthalmol. 252:1071-1078.
12. Eljarrat-Binstock E., Domb A. J. 2006. Iontophoresis: a non-invasive ocular drug delivery. J Control Release. 110:479-489.
13. Izumi-Nagai K., Nagai N., Ohgami K., Satofuka S., Ozawa Y., Tsubota K., Umezawa K., Ohno S., Oike Y., Ishida S. 2007. Macular pigment lutein is antiinflammatory in preventing choroidal neovascularization. Arterioscler Thromb Vasc Biol. 27:2555-2562.
14. Patane M. A., Cohen A., From S., Torkildsen G., Welch D., Ousler G. W., 3rd. 2011. Ocular iontophoresis of EGP-437 (dexamethasone phosphate) in dry eye patients: results of a randomized clinical trial. Clin Ophthalmol. 5:633-643.
15. Cohen A. E., Assang C., Patane M. A., From S., Korenfeld M., Avion Study I. 2012. Evaluation of dexamethasone phosphate delivered by ocular iontophoresis for treating noninfectious anterior uveitis. Ophthalmology. 119:66-73.
16. Tan C., Xia S., Xue J., Xie J., Feng B., Zhang X. 2013. Liposomes as vehicles for lutein: preparation, stability, liposomal membrane dynamics, and structure. J Agric Food Chem. 61:8175-8184.
17. French Decree no 2013-118. 2013 European directive 2010/63/UE. J. Offic. Rep. Fr Text 24 out of 130.
18. ASSOCIATION FOR RESEARCH IN VISION AND OPHTHALMOLOGY (ARVO). 1995. Statement for the Use of Animals in Ophthalmic and Vision Research.
19. Ratnapriya R., Chew E. Y. 2013. Age-related macular degeneration-clinical review and genetics update. Clin Genet. 84:160-166.
20. Age-Related Eye Disease Study 2 Research G. 2013. Lutein+ zeaxanthin and omega-3 fatty acids for age-related macular degeneration: the Age-Related Eye Disease Study 2 (AREDS2) randomized clinical trial. JAMA. 309:2005-2015.
21. Richer S., Stiles W., Statkute L., Pulido J., Frankowski J., Rudy D., Pei K., Tsipursky M., Nyland J. 2004. Double-masked, placebo-controlled, randomized trial of lutein and antioxidant supplementation in the intervention of atrophic age-related macular degeneration: the Veterans LAST study (Lutein Antioxidant Supplementation Trial). Optometry. 75:216-230.
22. Zhao L., Sweet B. V. 2008. Lutein and zeaxanthin for macular degeneration. Am J Health Syst Pharm. 65:1232-1238.
23. Simunovic M. P., Rush R. B., Hunyor A. P., Chang A. A. 2012. Endophthalmitis following intravitreal injection versus endophthalmitis following cataract surgery: clinical features, causative organisms and post-treatment outcomes. Br J Ophthalmol. 96:862-866.
24. Irigoyen C., Ziahosseini K., Morphis G., Stappler T., Heimann H. 2012. Endophthalmitis following intravitreal injections. Graefes Arch Clin Exp Ophthalmol. 250:499-505.
25. Patane M. A., Schubert W., Sanford T., Gee R., Burgos M., Isom W. P., Ruiz-Perez B. 2013. Evaluation of ocular and general safety following repeated dosing of dexamethasone phosphate delivered by transscleral iontophoresis in rabbits. J Ocul Pharmacol Ther. 29:760-769.
26. Patane M. A., Cohen A., Assang C., From S. 2010. Randomized, double-masked study of EGP-437 in subjects with non-infectious anterior segment uveitis. Poster presented at: American Academy of Ophthalmology annual meeting.
27. Halhal M., Renard G., Courtois Y., BenEzra D., Behar-Cohen F. 2004. Iontophoresis: from the lab to the bed side. Exp Eye Res. 78:751-757.
28. Horwath-Winter J., Schmut O., Haller-Schober E. M., Gruber A., Rieger G. 2005. Iodide iontophoresis as a treatment for dry eye syndrome. Br J Ophthalmol. 89:40-44.
29. Arboleda A., Kowalczuk L., Savoldelli M., Klein C., Ladraa S., Naud M. C., Aguilar M. C., Parel J. M., Behar-Cohen F. 2014. Evaluating in vivo delivery of riboflavin with coulomb-controlled iontophoresis for corneal collagen cross-linking: a pilot study. Invest Ophthalmol Vis Sci. 55:2731-2738.
30. Lim L. S., Mitchell P., Seddon J. M., Holz F. G., Wong T. Y. Age-related macular degeneration. The Lancet. 379:1728-1738.
31. de Jong P. T. V. M. 2006. Age-Related Macular Degeneration. New England Journal of Medicine. 355:1474-1485.
32. Jager R. D., Mieler W. F., Miller J. W. 2008. Age-Related Macular Degeneration. New England Journal of Medicine. 358:2606-2617.
33. Irigoyen C., Ziahosseini K., Morphis G., Stappler T., Heimann H. 2012. Endophthalmitis following intravitreal injections. Graefes Arch Clin Exp Ophthalmol. 250:499-505.
34. Ozawa Y., Sasaki M., Takahashi N., Kamoshita M., Miyake S., Tsubota K. 2012. Neuroprotective effects of lutein in the retina. Curr Pharm Des. 18:51-56.
35. Sasaki M., Ozawa Y., Kurihara T., Noda K., Imamura Y., Kobayashi S., Ishida S., Tsubota K. 2009. Neuroprotective effect of an antioxidant, lutein, during retinal inflammation. Invest Ophthalmol Vis Sci. 50:1433-1439.

36. Woo T. T., Li S. Y., Lai W. W., Wong D., Lo A. C. 2013. Neuroprotective effects of lutein in a rat model of retinal detachment. Graefes Arch Clin Exp Ophthalmol. 251:41-51.
37. Friedman D. S., O'Colmain B. J., Munoz B., Tomany S. C., McCarty C., de Jong P. T., Nemesure B., Mitchell P., Kempen J., Eye Diseases Prevalence Research G. 2004. Prevalence of age-related macular degeneration in the United States. Arch Ophthalmol. 122:564-572.
38. Eljarrat-Binstock E., Orucov F., Aldouby Y., Frucht-Pery J., Domb A. J. 2008. Charged nanoparticles delivery to the eye using hydrogel iontophoresis. J Control Release. 126:156-161.
39. Gungor S., Delgado-Charro M. B., Ruiz-Perez B., Schubert W., Isom P., Moslemy P., Patane M. A., Guy R. H. 2010. Trans-scleral iontophoretic delivery of low molecular weight therapeutics. J Control Release. 147:225-231.
40. Pascolini D., Mariotti S. P., Pokharel G. P., Pararajasegaram R., Etya'ale D., Negrel A. D., Resnikoff S. 2004. 2002 global update of available data on visual impairment: a compilation of population-based prevalence studies. Ophthalmic Epidemiol. 11:67-115.
41. Congdon N., O'Colmain B., Klaver C. C., Klein R., Munoz B., Friedman D. S., Kempen J., Taylor H. R., Mitchell P., Eye Diseases Prevalence Research G. 2004. Causes and prevalence of visual impairment among adults in the United States. Arch Ophthalmol. 122:477-485.
42. Seddon J. M., Ajani U. A., Sperduto R. D., Hiller R., Blair N., Burton T. C., Farber M. D., Gragoudas E. S., Haller J., Miller D. T., et al. 1994. Dietary carotenoids, vitamins A, C, and E, and advanced age-related macular degeneration. Eye Disease Case-Control Study Group. JAMA. 272:1413-1420.
43. van de Kraats J., Kanis M. J., Genders S. W., van Norren D. 2008. Lutein and zeaxanthin measured separately in the living human retina with fundus reflectometry. Invest Ophthalmol Vis Sci. 49:5568-5573.
44. Barker F. M., 2nd, Snodderly D. M., Johnson E. J., Schalch W., Koepcke W., Gerss J., Neuringer M. 2011. Nutritional manipulation of primate retinas, V: effects of lutein, zeaxanthin, and n-3 fatty acids on retinal sensitivity to blue-light-induced damage. Invest Ophthalmol Vis Sci. 52:3934-3942.
45. Cunha-Vaz J., Bernardes R., Lobo C. 2011. Blood-retinal barrier. Eur J Ophthalmol. 21 Suppl 6:S3-9.
46. Prausnitz M. R., Noonan J. S. 1998. Permeability of cornea, sclera, and conjunctiva: a literature analysis for drug delivery to the eye. J Pharm Sci. 87:1479-1488.
47. www.jove.com/video/3765

We claim:

1. A method of depositing at least one carotenoid in ocular tissues, comprising the steps of formulating a liposome having a positive zeta potential containing the at least one carotenoid in an amount effective to increase macular pigment in the ocular tissues of a subject, charging an iontophoresis device with a composition of the liposome containing at least one carotenoid, applying the iontophoresis device to the eye of the subject, and operating the iontophoresis device, wherein the at least one carotenoid is selected from the group consisting of lutein and zeaxanthin.

2. A method of treating or ameliorating age-related macular degeneration, comprising the steps of formulating a liposome having a positive zeta potential containing at least one carotenoid in an amount effective to increase macular pigment in the ocular tissues of a subject, charging an iontophoresis device with a composition of the liposome, applying the iontophoresis device to the eye of a subject, and operating the iontophoresis device, wherein the at least one carotenoid is selected from the group consisting of lutein and zeaxanthin.

3. The method of claim 2, wherein treating or ameliorating age-related macular degeneration is preventing or delaying the progression of age-related macular degeneration.

\* \* \* \* \*